United States Patent [19]

Wong et al.

[11] Patent Number: 5,403,726
[45] Date of Patent: Apr. 4, 1995

[54] ENZYMATIC PROCESS FOR PRODUCING A GALACTOSYL$\beta$1,3GLYCAL DISACCARIDE USING $\beta$-GALACTOSIDASE

[75] Inventors: Chi-Huey Wong, Rancho Santa Fe; Gary C. Look, Sunnyvale, both of Calif.

[73] Assignee: The Scripps Research Institute, La Jolla, Calif.

[21] Appl. No.: 915,465

[22] Filed: Jul. 16, 1992

Related U.S. Application Data

[63] Continuation-in-part of Ser. No. 910,612, Jul. 8, 1992, abandoned, and Ser. No. 889,652, May 26, 1992, which is a continuation-in-part of Ser. No. 852,409, Mar. 16, 1992, abandoned, which is a continuation-in-part of Ser. No. 738,211, Jul. 30, 1991, abandoned, said Ser. No. 910,612, is a continuation-in-part of Ser. No. 901,260, Jun. 19, 1992, abandoned, which is a continuation-in-part of Ser. No. 777,662, Oct. 15, 1991, abandoned.

[51] Int. Cl.$^6$ .................... C12P 19/12; C12N 9/38
[52] U.S. Cl. ..................... 435/100; 435/207
[58] Field of Search ................. 435/100, 207

[56] References Cited

U.S. PATENT DOCUMENTS

| | | | |
|---|---|---|---|
| 4,918,009 | 4/1990 | Nilsson | 435/73 |
| 5,180,674 | 1/1993 | Roth | 435/288 |
| 5,246,840 | 9/1993 | Nilsson | 435/101 |

OTHER PUBLICATIONS

Distler et al., *Complex Carbohydrates*, Edited by Victor Ginsburg, Methods in Enzymology, pp. 514–520, 1978.
Leppänen et al., Biochemistry, 1991, 30, 9287–9296.
Petit et al., Tetrahedron Letters, vol. 32, No. 43, 6125–6128, 1991.
Cummings et al., J. of Biol. Chem., vol. 259, No. 10, 6253–6260, 1984.
Presant et al., J. of Biol. Chem., vol. 247, No. 21, 6937–45, 1972.
Distler et al., J. of Biol. Chem., vol. 248, No. 19, 6772–6780, 1973.
Vandenheede et al., J. of Biol. Chem., vol. 247, No. 24, 7885–7889, 1972.
Sheares et al., J. of Biol. Chem., vol. 257, No. 2, 599–602, 1982.
Toone et al., Tetrahedron, 45(17), 5365–5422, 1989.
Lehmann et al., Carbohydrate Research, 58(1977), 73–78.
Nilsson, Tibtech, 1988, vol. 6, pp. 256–264.
Lehmann et al., Carbohydrate Research, 23(1972), 359–368.
Lehmann et al., Carbohydrate Research, 58(1977), 65–72.
Legler, Advances in Carbohydrate Chemistry and Biochemistry, vol. 48, pp. 319–384, 1990.
Sinnott, Chem. Rev., 1990, 90, 1171–4202.
Kaila et al., J. Org. Chem., 1992, 57, 4576–4578.
Dettinger et al., Carbohydrate Research, 74(1979), 301–307.
Dean et al., J. of Biol. Chem., vol. 254, No. 20, pp. 10006–10010, 1979.
Sandermann, Jr., Eur. J. Biochem., 80, 507–515, 1977.
Karz et al., Carbohydrate Research, 93(1981), C14–C20.
Nilsson, Carbohydrate Research, 167, 1987, pp. 95–103.
Nilsson, Ann. N. Y. Acad. Sci., 542 (Enzyme Eng. 9), 1988, 383–9.
Nilsson, *Carbohyd. Res.*, 188:9–17 (1989).

*Primary Examiner*—David M. Naff
*Assistant Examiner*—Mike Meller
*Attorney, Agent, or Firm*—Welsh & Katz, Ltd.

[57] ABSTRACT

An enzymatic process is disclosed for the preparation of galactosyl$\beta$1,3glycal disaccharides such as Gal$\beta$1,3-Glucal, an intermediate useful in Le$^a$ preparation and an inhibitor of $\beta$-galactosidase. The process utilizes $\beta$-galactosidase, an enzyme usually used for bond breaking, to form a bond between a galactoside and a glucal such as glycal, a 6-O—$C_1$-$C_6$ acylglucal or 6-O—$C_1$-$C_6$ acetylgalactal.

13 Claims, No Drawings

ENZYMATIC PROCESS FOR PRODUCING A GALACTOSYLβ1,3GLYCAL DISACCHARIDE USING β-GALACTOSIDASE

This invention was made with government support under Contract No. GM 44154 awarded by the National Institutes of Health. The government has certain rights in the invention.

This application is a continuation-in-part of U.S. patent application Ser. No. 910,612, filed Jul. 8, 1992, now abandoned, and U.S. patent application Ser. No. 889,652, filed May 26, 1992, wherein 910,612 is a continuation-in-part of U.S. patent application Ser. No. 901,260, filed Jun. 19, 1992, now abandoned, which is a continuation-in-part of U.S. Pat. Ser. No. 777,662, filed Oct. 15, 1991, now abandoned, and U.S. patent application Ser. No. 889,652 is a continuation-in-part of U.S. patent application Ser. No. 852,409, filed Mar. 16, 1992, now abandoned, which is a continuation-in-part of Ser. No. 738,211, filed Jul. 30, 1991, now abandoned, whose disclosures are incorporated herein by reference.

DESCRIPTION

1. Technical Field

The present invention relates to the synthesis of Le$^a$ and sialyl Le$^a$ and analogs thereof, and more particularly to the synthesis of a galactosylβ1,3glycal that is a galactosidase inhibitor and is also an intermediate that can be used in the syntheses of Le$^a$, sialyl Le$^a$ and analogs thereof.

2. Background Art

Disaccharides possessing a β1,3-linkage are important core units in the blood group determinants, tumor associated antigens, and the ligands of adhesion molecules. [Hakomori, Adv. Cancer Res., 52:257 (1981); Fenzi, Nature, 314:53 (1985); Berg et al., J. Biol. Chem., 266:14869 (1991); Hodgson, Biotechnology, 9:609 (1991)]. For example, Le$^a$ and Sialyl Le$^a$ incorporate the Type I (Galβ1,3GlcNAc) subunit (shown below) in its structure. [Fenzi, Nature, 314:53 (1985)].

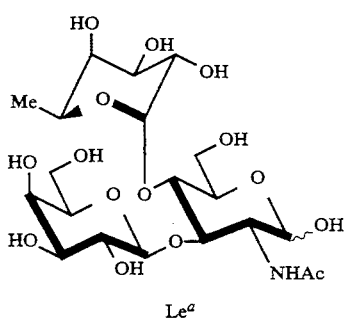

Le$^a$

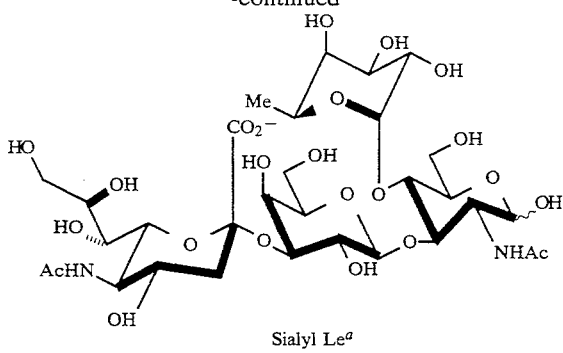

Sialyl Le$^a$

These types of compounds and their derivatives or analogs are important tools for the study of cell-cell interactions and have been the objects of synthetic effort. [Wong et al., J. Carbohydr. Chem., 9:745 (1990); Sabesan et al., Can. J. Chem., 62:644 (1984); Jacquinet et al., Tetrahedron Lett., 22:15, 1387 (1981)]. However, chemical syntheses require many protecting group manipulations in order to obtain the desired regioselectivity.

Although no β1,3-linkage forming glycosyltransferases have been isolated, glycosidases Nilsson, Trends Biotechnol., 6:256 (1988), and references therein; Toone et al., Tetrahedron, 4.5:5365 (1989); Cote et al., Glvcoconjugate J., 7:145 (1990); David et al., Adv. Carbohydr. Biochem., 49:175 (1991)] previously have been used to form β1,3-linked disaccharides through the use of less readliy available enzymes [Hedbys et al., Glyconconjugate J., 6:161 (1989)] and by the manipulation of the anomeric protecting group of the acceptor species. [Nilsson, Trends biotechnol., 6256 (1988)].

Glycals have been examined by Lehmann et al. [Brockhaus et al., J. Carbohydr. Res., 53:21 (1977); Lehmann et al., Carbohydr. Res., 58:65 (1977); Lehmann et al., Carbohydr. Res., 58:72 (1977)] in glycosidase-mediated coupling reactions. Those investigators determined that glucal in the presence of emulsin β-glucosidase forms 2-deoxy-Gluβ1,3-glucal in up to 50 percent yield. In addition, incubation of D-galactal in the presence of glycol or water and β-galactosidase formed the corresponding glycosides via addition across the double bond. D-Glucal was reported to react similarly in the presence of β-glucosidase.

Lehmann [Brockhaus et al., J. Carbohydr. Res., 53:21 (1977); Lehmann et al., Carbohydr. Res., 58:65 (1977); Lehmann et al., Carbohydr. Res., 58:72 (1977)] and others have also used glucal as a donor to form 2-deoxy glycosides [Wang et al., Carbohydr. Res., 219:133 (1991); Priebe et al., Tetrahedron Lett., 32:3313 (1991); Horton et al., Carbohydr. Res., 205:71 (1990); Lemieux et al., Can J, Chem., 57:1244 (1979); Schaubach et al., Liebigs Ann. Chem., 607 (1991); Gervay et al., J. Org. Chem., 56:5448 (1991)] have also used glucal as a donor to form 2-deoxy-glycosides.

A product produced by the process described herein is an intermediate for the preparation of pharmaceutically active carbohydrates. Such carbohydrates include sialyl Lewis ligands. Sialyl Lewis ligands are defined as any compound that binds to a selecting receptor as described in Polley, et al., Proc. Natl,.Acad. Sci., U.S.A., 88:6224–6228 (1991). These ligands are typified by their sialic acid- and fucose-containing terminal structures found on glycoproteins and glycolipids. These ligands include the naturally occurring ligands sialyl Le$^x$ (SLe$^x$) and sialyl Le$^a$ (SLe$^a$). These ligands further include unnatural analogs that bind in a similar manner to the natural receptors of the ligands. For example, ligand analogs can be made with acceptor oligosaccharide analogs for glycosyltransferases, as discussed elsewhere. Several acceptor analogs are well known and include the deoxygenated oligosaccharides described in Hindsgaul et. al., *J. Biol. Chem.*, 266:17858–17862 (1991). Sialyl Le$^a$ and its analogs are the ligands of interest here as pharmaceutically active carbohydrates.

It was desired to develop an efficient general entry into the β1,3-linked galactosyl glycal disaccharides through the use of enzymes. The disclosure that follows illustrates the facile galactosidase-mediated syntheses of the desired β1,3-linked disaccharides using an unprotected galactoside donor molecule and an unprotected glucal or a 6-O—C$_1$-C$_6$ acyl glucal or galactal acceptor.

BRIEF SUMMARY OF THE INVENTION

The present invention contemplates a process for the preparation of a galactosylβ1,3glycal disaccharide. In accordance with this process, (i) a galactoside donor molecule, (ii) glucal, a 6-O—C$_1$-C$_6$ acyl glucal or a 6-O—C$_1$-C$_6$ acyl galactal as acceptor and (iii) a catalytic amount of β-galactosidase are admixed in an aqueous medium to form an admixture. That admixture is maintained under biological reaction conditions for a time period sufficient to form the galactosylβ1,3glycal disaccharide.

The galactoside donor is preferably an activated galactoside such as p-nitrophenyl galactopyranoside. The acceptor is preferably substituted at its 6-position by a C$_1$-C$_6$ acyl group. Acetyl (Ac) is a preferred C$_1$-C$_6$ acyl group. The galactosylβ1,3glycal is preferably recovered after it is formed.

The present invention has several benefits and advantages.

One benefit is that costly protection and deprotection steps are not required for the starting materials and products in obtaining a stereoselective synthesis. Thus, the galactoside is free from any groups on its ring carbons or hydroxyls other than hydrogen. Similarly, glucal can be used without protecting groups, although a 6-O—C$_1$-C$_6$ acyl glucal or galactal as can be readily and inexpensively prepared and thereafter removed, are preferred glycal acceptors.

An advantage of this invention is that it utilizes an inexpensive enzyme such as *E. coli* β-galactosidase to carry out the synthesis.

Another benefit is that the reaction is relatively free of side reaction products so that recovery of the products is relatively straightforward. This is particularly the case where a 6-O—C$_1$-C$_6$ acyl glucal or galactal are used as the resulting β1,3disaccharide is the only disaccharide formed.

Another advantage of this invention is that the disaccharide products are obtained in relatively high yields of about 40–50 percent.

Still further benefits and advantages will be apparent to the skilled worker from the disclosures that follow.

Oligosaccharides are considered to have a reducing end and a non-reducing end, whether or not the saccharide at the reducing end is in fact a reducing sugar. In accordance with accepted nomenclature, oligosaccharides are depicted herein with the non-reducing end on the left and the reducing end on the right.

All oligosaccharides described herein are, thus, described with the name or abbreviation for the non-reducing saccharide (i.e., Gal), followed by the configuration of the glycosidic bond (α or β), the ring position of the non-reducing saccharide involved in the bond (1), the ring position of the reducing saccharide involved in the bond (3 or 6), and then the name or abbreviation of the reducing saccharide (i.e., Glucal).

DETAILED DESCRIPTION OF THE INVENTION

The use of glycals as acceptors for the enzyme-mediated formation of β1,3 linked galactosyl glycal disaccharides has been investigated. The resultant 1,2-anhydro disaccharides can subsequently be transformed into a variety of derivatives as readily demonstrated by several research groups. [Wang et al., *Carbohydr. Res.*, 219:133 (1991); Priebe et al., *Tetrahedron Lett.*, 32:3313 (1991); Horton et al., *Carbohydr. Res.*, 205:71 (1990); Lemieux et al., *Can J. Chem.*, 57:1244 (1979); Schaubach et al., *Liebigs Ann. Chem.*, 607 (1991); Gervay et al., *J. Org. Chem.*, 56:5448 (1991); Petit et al., *Tetrahedron Lett.*, 32:6125 (1991)].

For example, Galβ1,3Glucal can be transformed by azido nitration [Lemieux et al, *Can J. Chem.*, 57:1244 (1979)] to Galβ1,3GlcNAc. This compound can then be enzymatically fucosylated [Dumas et al., *BioMed. Chem. Lett.*, 1:425 (1991); Palcic et al., *Carbohydr. Res.*, 190:1 (1989)] or sialylated [Sebesan et al., *J. Am. Chem. Soc.*, 108:2068 (1986)] and fucosylated to afford Le$^a$ or sialyl Le$^a$. Galβ1,3Galactal can be similarly transformed into Galβ1,3GalNAc, which is present in porcine mucin and as a surface marker on some tumors.

The resulting Le$^a$ or sialyl Le$^a$ can then be linked to a carrier protein such as KLH via its reducing end 1-position hydroxyl to form a synthetic immunogen. That immunogen can thereafter be used to induce antibodies that immunoreact with Le$^a$ or sialyl Le$^a$.

In another example, Galβ1,3Glucal can be reacted with chloroperoxidase, hydrogen peroxide, a halide salt such as KCl, KBr or KI in an aqueous buffer at about pH 3 to form the corresponding Galβ1,3(2-deoxy-2-halo)Glc that can then be further fucosylated and sialyated as discussed above to form the 2-halo-Le$^a$ and 2-halo-sialyl Le$^a$ analogs. Alternatively, Galβ1,3Glucal can be sialylated and fucosylated and then reacted with chloroperoxidase as discussed above to prepare the 2-halo Le$^a$ analog.

The present invention thus provides a process for the preparation of a galactosylβ1,3glycal disaccharide such as β1,3lactal (Galβ1,3Glucal), Galβ1,3(6-O—C$_1$-C$_6$acyl)glucal or Galβ1,3(6-O-C$_1$C$_6$acyl)galactal. In accordance with that method, (i) a galactoside donor molecule is admixed with (ii) a glycal such as glucal, 6-O—C$_1$-C$_6$ acyl glucal or 6-O—C$_1$-C$_6$ acyl galactal as an acceptor and (iii) a catalytic amount of β-galactosidase in an aqueous medium to form an admixture. The admixture so formed is maintained under biological reaction conditions for a time period sufficient to form the galactosylβ1,3glycal disaccharide.

The galactoside donor molecule used is preferably an activated β-galactoside; i.e., a galactose molecule β-bonded at its 1-position to a good leaving group. An exemplary activated galactoside is β-p-nitrophenyl galactopyranoside (GalβpNo$_2$Ph), Compound 1. Other activating 1-position groups include phenyl, methyl, methoxymethyl and methoxyethyl ethers, and the fluoro group linked directly to the 1-position galactosyl carbon. Additional activating groups well known in the art are discussed in Nilsson et al., *Trends. Biotechnol.*, 6:256 (1988) and the citations therein. A non-activated galactoside donor such as lactose (Galβ1,4Glu) can also be utilized, but are less preferred because their use provides product mixtures. Aside from the 1-position group of the galactoside donor molecule, that molecule is free from other groups bonded to its carbon atom chain (other than hydrogens) or hydroxyls; i.e., an unsubstituted galactoside donor molecule is utilized.

The glycal acceptor molecule utilized is glucal itself, a 6-O—$C_1$-$C_6$ acyl glucal or a 6-O—$C_1$-$C_6$ acyl galactal. As illustrated hereinafter, galactal cannot be used in this reaction as it is an inhibitor, whereas a 6-O—$C_1$-$C_6$ acyl galactal is an efficient substrate whose use provides but one galactosylβ1,3galactal disaccharide product.

Exemplary 6-O—$C_1$-$C_6$ acyl glucals or galactals contain a $C_1$-$C_6$ acyl group such as formyl, acetyl, 2-butanoyl, hexanoyl groups and the like bonded to the oxygen atom at the 6-position of the carbon chain. Of the $C_1$-$C_6$ acyl groups, acetyl is particularly preferred. Aside from the presence of a 6-O—$C_1$-$C_6$ acyl group, which presence is preferred, the carbons and hydroxyls of the glucal or acyl galactal are otherwise also unsubstituted.

The β-galactosidase utilized can be from any source. The readily available, inexpensive *E. coli* β-galactosidase [EC 3.2.1.23] has been utilized herein as illustrative, and is a preferred enzyme. Several galactosidase enzyme preparations of varying activity against Compound 1 are available from Sigma Chemical Co., St. Louis, Mo., USA, and can be used.

β-Galactosidase appears to be a unique enzyme for carrying out this reaction. For example, β-glucosidase and β-N-acetylglucosaminidase could not be used successfully, and their use led to hydrolytic products rather than a desired galactosyl disaccharide.

The β-galactosidase is present in a catalytic amount. As used herein, the phrase "catalytic amount" means that amount of an enzyme at least sufficient to catalyze, in a non-rate limiting manner, the conversion of that enzyme's substrate to product.

The catalytic amount of a particular enzyme varies according to the concentration of that enzyme's donor and acceptor substrates as well as to reaction conditions such as temperature, time and pH value. Means for determining the catalytic amount for a given enzyme under preselected substrate concentrations and reaction conditions are well known to those of skill in the art. Typical amounts of β-galactosidase are noted hereinafter.

Admixing comprises mixing each ingredient with each of the other ingredients in a suitable aqueous medium (solvent) to form a reaction mixture. The aqueous medium can include up to about 50 volume percent of a water miscible organic solvent such as acetone. The reaction mixture is maintained under biological reaction conditions of temperature, pH, solvent osmolality, ionic composition and ambient atmospheric pressure (as described herein) for a period of time sufficient to form the desired galactosyl glycal disaccharide.

The use of acetone cosolvent in glycosidase-mediated reactions previously has been examined by Petit and coworkers [Petit et al., *Tetrahedron Lett.*, 32:6125 (1991)]. Acetone can be present at up to about 50 volume percent, but it is preferred to use about 3 to about 5 volume percent because of the observed slowing down of the reaction rate. A similarly small amount of acetonitrile can also be used.

Temperature can range from about 15° C. to about 40° C. Preferably the temperature is about 20° C. to about 40° C. and, more preferably about 25° C. to about 37° C.

The pH value can range from about 6.0 to about 11.0. Preferably, the pH value is from about 6.0 to about 8.0 and, more preferably about 6.0 to about 7.0. The pH value is maintained by buffers in the aqueous solvent. The buffer is devoid of chelators that bind enzyme cofactors such as $Mg^{+2}$ or $Mn^{+2}$. The selection of a buffer is based on the ability of the buffer to maintain pH value at the desired level.

The osmolality and ionic composition of the aqueous solvent are designed and selected to solubilize the ingredients of the reaction mixture and to provide cofactors for the enzymes contained in the reaction mixture. The osmolality of the aqueous solvent including the buffer is preferably from about 100 mOsm to about 300 mOsm.

Typical reaction times are about one-half day to about two days at ambient room temperature. Where yields are to be maximized, a reaction time of about one day (about 24 hours) is typically used. Where Compound 1 is used as the galactoside donor molecule, the reaction can be run until no further p-nitrophenol is produced or that production is diminished to the background hydrolytic rate.

The products of the reaction are preferably recovered at the end of the reaction. That recovery can be by usual techniques of organic chemistry such as column chromatography or high pressure liquid chromatography. The reaction products can also be derivatized as by acetylation prior to that recovery to facilitate the recovery and purification. The acetyl groups can be readily removed by reaction with a suitable base such as ammonia or an alkoxide ion such as methoxide. The reaction product can also be reacted further without recovery, but such further reactions are not preferred as complex mixtures that are difficult to separate can result.

Results

To increase the yield of disaccharide, activated donors were used illustratively here in the kinetic method of glycosidic bond formation. [Nilsson, I. *Trends Biotechnol.*, 6:256 (1988) and the citations therein]. Disaccharide formation was initially examined using commercially available *E. coli* β-galactosidase [EC 3.2.1.23] and 4-nitrophenyl β-galactopyranoside (Compound 1) as the galactose donor and glucal (Compound 2) [Hodgson, *Biotechnology*, 9:609 (1991)] as the acceptor. The reaction was monitored by thin layer chromatograph (TLC). After no additional nitrophenyl galactoside appeared to be consumed (19-26 hours), the reaction was terminated.

For simplification of isolation and subsequent identification, the crude reaction mixture residue was concentrated and directly acetylated [step 2 of Scheme 1, below, using acetic anhydride ($Ac_2O$) and pyridine (pyr)] to provide the product β1,3 and β1,6 hexaacetates, Compounds 3 and 4, respectively. Silica gel chromatography easily separated the peracetylated products from the starting materials. This reaction is illustrated below in Scheme 1.

Scheme 1

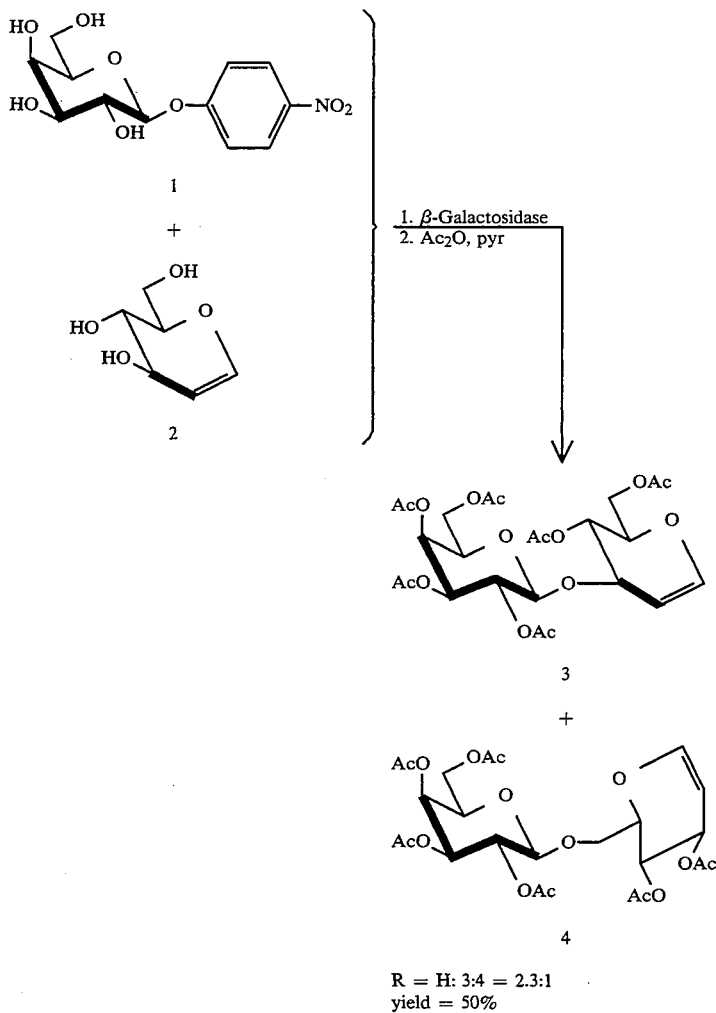

R = H: 3:4 = 2.3:1
yield = 50%

$^1$H NMR analysis of the purified disaccharide fraction indicated a 2.3:1 mixture of Galβ1,3Glucal and Galβ1,6Glucal. No Galβ1,4Glucal product was observed. That product distribution is atypical of the *E. coli* enzyme that normally forms a β1,6 isomer in preference to other regioisomers. [David et al., *Adv. Carbohydr. Biochem.*, 49:175 (1991)]. The deacylated compounds can be readily prepared from the hexaacetate by known methods.

In a typical procedure, Compound 1 (77 mg, 0.26 mmol) and Compound a (54 mg, 0.36 mmol) were combined at 25° C. with *E. coli* β-galactosidase (75 units) in 4 mL of a 0.07 M PIPES/0.2M NaOAc/0.1M EDTA solution at pH 6.5. The progress of the reaction was monitored by TLC (silica gel, 7:2:1 iPrOH—NH$_4$OH—H$_2$O). After 26 hours, the solvent was removed in vacuo and the residue treated with acetic anhydride (2 mL) and pyridine (2 mL). After an additional 12 hours, the mixture was concentrated in vacuo and the residue purified by silica gel chromatography (2:3 ethyl acetate-hexanes) to afford a 2.3:1 mixture of β-1,3 and β-1,6 isomers (72 mg, 50 percent). Also isolated were the peracetates of Compounds 1 and 2. The position of the glycoside linkage was unambiguously determined by $^1$H NMR decoupling studies.

When acetone was used as a cosolvent (3 volume percent) a 50 percent yield of the β1,3 and β1,6 isomers was obtained in the same ratio.

The Galβ1,3Glucal and Galβ1,6Glucal mixture is an inhibitor of β-galactosidase with an IC$_{50}$ of about 17 mM as determined versus Compound 1, indicating the problem of product inhibition.

The use of 6-O-acetylated glucal (Compound 6) next was examined as a possible acceptor in order to force the specific formation of the β1,3 linkage. Glycoside acceptors chemically modified at positions other than C-1 have not been studied as substrates for glycosidase-mediated coupling reactions.

The 6-O-acylated glucal was prepared as described previously through the use of a lipase- or protease-mediated monoacylation reaction. [Holla et al., *Angew. Chem., Int,. Ed. Enal.,* 28:220 (1989); Zhong et al., *J. Am. Chem. Soc.*, 113:683 (1991); Wang et al., *Tetrahedron Lett.*, 30:1917 (1989); Riva et al., *J. Am. Chem. Soc.*, 110:584 (1988)]. Treatment of the monoacetylated glucal for 17 hours with Compound 1 in the presence of β-galactosidase from *E. coli*, followed by peracylation afforded Compound 3 in 42 percent yield as the exclusive disaccharide product.

The monoacetylated Galβ1,3(6-O-Ac)Glucal (Compound 5) can be isolated partially pure by silica gel chromatography using 5:2:2 CHCl₃:ethyl acetate: methanol as the eluant. This reaction is shown in Scheme 2, below.

ever, enzyme activity was not lost as addition of lactose to the reaction mixture initiated product formation. This observation can be explained if glucal is bound in

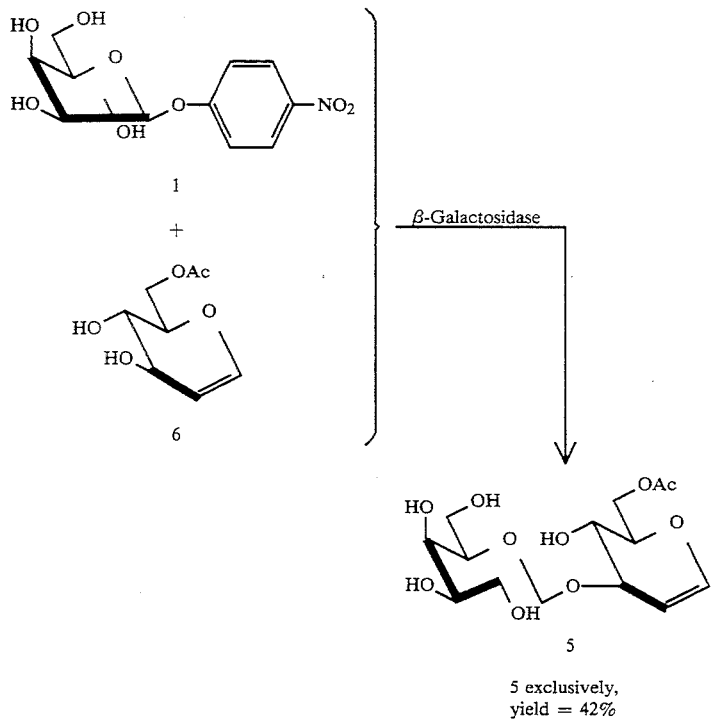

Scheme 2

5 exclusively,
yield = 42%

In an effort to use a less expensive galactoside source, β-lactose was examined under enzymatic conditions as the galactoside donor molecule. Whereas disaccharide formation was observed, the reaction mixture was more complicated and purification of the products proved difficult. Interestingly, when lactal [Haworth et al., *J. Chem. Soc.*, 2644 (1930)] (Galβ1,4Glucal) was used as the galactoside source as well as the glucal source, rapid hydrolysis to the monosaccharides occurred (<4 hours). However, no disaccharide products were observed.

Stoichiometric amounts of glucal in combination with lactal also failed to produce disaccharides. However, enzyme activity was not lost as addition of lactose to the reaction mixture initiated product formation. This observation can be explained if glucal is bound in the active site better than galactose but worse than the disaccharides. The activated galactose moiety may diffuse from the active site (as galactose) before product formation can occur when lactal is used as the substrate.

Galactal (Compound 7) was also examined as a potential acceptor. That molecule acted as an inhibitor and provided no reaction product. This is noted in Table 1 hereinafter. However, 6-O-acetyl galactal (Compound 8; prepared as was Compound 6) proved to be a good substrate and provided the corresponding Galβ1,3-(6-O-Ac)Galactal (Compound 9) in 42 percent yield as the only galactosyl glycal disaccharide. This reaction is shown in Scheme 3, below.

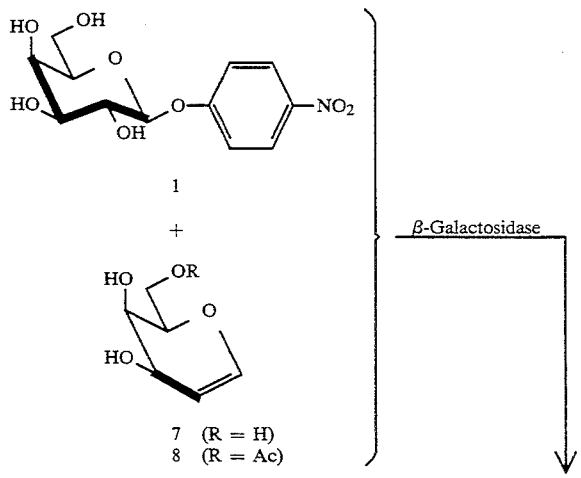

Scheme 3

7 (R = H)
8 (R = Ac)

Scheme 3

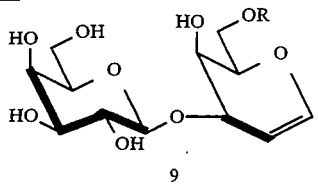

9

R = H: No Reaction
R = Ac: 9 exclusively,
yield = 42%

Several other glycosidases and glycals were examined for enzymatic coupling and these results are presented in Table 1, below. Galactal and fucal were apparently poor acceptors for the glycosidases. [Lee, Biochem. Biophys. Res. Commun., 35:161 (1969)].

TABLE 1

| Glycosidase-Mediated Coupling Reactions[#] | | | |
|---|---|---|---|
| Enzyme (Source) | Donor | Acceptor | Peracylated Products (Yield) |
| β-Galactosidase (E. coli) | GalβpNo$_2$Ph | Glucal | Galβ1,3Glucal (35%) β- and Galβ1,6Glucal (15%) |
| β-Galactosidase (E. coli) | GalβpNO$_2$Ph | Galactal | No reaction |
| β-Galactosidase (E. coli) | GalβpNO$_2$Ph | Fucal | Hydrolysis to Gal |
| β-Galactosidase (E. coli) | GalβpNO$_2$Ph | 6-O-acetyl Glucal | Galβ1,3-(6-O-Acetyl) Glucal (42%) |
| β-Galactosidase (E. coli) | lactose | Glucal | Galβ1,3Glucal and Galβ1,6Glucal |
| β-Galactosidase (E. coli) | GalβpNO$_2$Ph | 6-O-Acetyl Galactal | Galβ1,3-(6-O-Acetyl) Galactal (42%) |
| β-Glucosidase (almond) | GlcβpNO$_2$Ph | Galactal | Hydrolysis to Glc |
| β-Glucosidase (almond) | GlcβpNO$_2$Ph | Glucal | No reaction |
| β-Glucosidase (almond) | GlcβpNO$_2$Ph | Fucal | Hydrolysis to Glc |
| β-N-Acetylglucosaminidase (Jack Bean) | GlcNAcβpNO$_2$Ph | Glucal | Hydrolysis to GlcNAc |
| β-N-Acetylglucosaminidase (Jack Bean) | GlcNAcβpNO$_2$Ph | Galactal | Hydrolysis to GlcNAc |

[#]Each enzyme was used within its optimum pH range as recommended by Boehringer Mannheim, Biochemica Information, Keesev, J. ed., Boehringer Mannheim, Indianapolis, IN, 1987.

Inhibition Studies

The inhibition studies using β1,3lactal were conducted as described in Kajimoto et al., J. Am. Chem. Soc., 113:6178 (1991). Briefly, those studies were carried out as follows.

A. Preparation of solutions (a) PIPES-NaOAc buffer (0.07M PIPES, 0.2M NaOAc and 0.2 mM EDTA, pH 6.5). This buffer was prepared according to the literature procedure [Dale et al., Biochemistry, 24:3530 (1985)].

(b) β-D-Galactosidase (E. coli): The stock enzyme solution was prepared by dissolving sufficient enzyme in PIPES-NaOAc buffer solution to provide a solution at 1000 U/mL. This stock enzyme solution was diluted 5-fold for the enzymatic assay.

(c) Substrate solutions: substrates were dissolved in the corresponding buffer solution for enzymatic assay.

(d) For β-glucosidase and β-Nacetylglucosaminidase of Table 1, the following were used:
 (i) β-glucosidase in 50 mM NaOAc at pH 5.5; and
 (ii) β-Nacetylglucoaminidase in 0.05M citric acid, 0.03M NaOH at pH 4.6.

B. General Procedure for Enzyme Assay

For the IC$_{50}$ assay:

A solution of 4-nitrophenyl β-galactopyranoside substrate (20 μL of a 0.082M solution in PIPES/EDTA/NaOAc buffer, 1.64 μm in PIPES/EDTA/NaOAc buffer at pH 6.5 (960 μL) was prepared. The β-galactosidase solution (20 μL, 20 U) was added to the substrate solution. The solution was quickly mixed and the progress of hydrolysis was monitored at 400 nm at 23° C. for one minute. The above procedure was repeated with the addition of inhibitor (20, 40 and 200 μL of a 0.009M solution in PIPES/EDTA/NaOAc buffer) with a corresponding decrease in the amount of buffer solution of the substrate (940 to 860 μL) to maintain the reaction volume at 1 mL. The IC$_{50}$ value was then calculated from the resulting inhibition data.

Physical Data

Galβ1,3Glucal-O$_6$-hexacetate (Compound 3)

Data for 3: $^1$H NMR (500 MHz, CDCl$_3$) δ6.48 (d, J=6.37 Hz, 1H, Glucal H-1), 5.39 (d, J=3.43 Hz, 1H, Gal H-4), 5.23 (app t, J=3.71 Hz, 1H, Glucal H-4), 5.17 (dd, J=7.94, 10.46 Hz, 1H, Gal H-2), 5.02 (dd, J=3.43, 10.46 Hz, 1H, Gal H-3), 4.87 (app t, J=5.53 Hz, 1H, Glucal H-2), 4.66 (d, J=7.94 Hz, 1H, Gal H-1), 4.41 (dd, J=8.13, 12.06 Hz, 1H, Glucal H-6), 4.36–4.34 (m, 1H, Glucal H-3), 4.19–4.08 (m, 4H, Gal H-6, Glucal H-5,6), 3.93 (app t, J=6.68 Hz, 1H, Gal H-5), 2.17, 2.09, 2.09, 2.06, 2.05, 1.98 (s, 3H each, 6×OAc); $^{13}$C NMR (125 MHz, CDCl$_3$) 6 170.5, 170.4, 170.3, 170.1, 169.5, 169.3, 145.2, 99.1,97.1, 73.8, 70.9, 70.8, 69.3, 68.7, 67.9, 66.9, 61.5, 61.2, 29.7, 20.9, 20.8, 20.7, 20.7, 20.5; MS (CI, NaI) 583.1639 (583.1639 calcd for C$_{24}$H$_{32}$O$_{15}$Na, M+Na+).

Galβ1,3Glucal-6-O-Acetate (Compound 5)

The monoacetylated Galβ1,3Glucal can be isolated partially pure by silica gel chromatography using 5:2:2 CHCl$_3$:ethyl acetate: methanol as the eluant. Data for the monoacetate: $^1$H NMR (500 MHz, D$_2$O) δ 6.51 (d, J=6.10 Hz, 1H, Glucal H-1), 5.05–5.04 (m, 1H, Glucal H-2), 4.60 (d, J=7.95 Hz, 1H, Gal H-1), 4.47 (br d, 2H, Glucal H-6), 2.76 (m, 1H, Glucal H-3), 4.24–4.22 (m, 1H, Glucal H-5), 4.02 (t, J=6.37 Hz, 1 H, Glucal H-4), 3.86–3.76 (m, 3H, Gal H-5,6), 3.72–3.70 (m, 1H, Gal H-3), 3.56 (t, J=8.10 Hz, Gal H-2); $^{13}$C NMR (125 MHz, D$_2$O) δ174.5, 144.8, 101.8, 100.5, 76.3, 76.0, 75.7, 73.2, 71.1, 69.0, 67.3, 63.5, 61.5, 20.7; MS (CI, NaI) 373.1111 (373.1111 calcd for C$_{14}$H$_{22}$O$_{10}$Na, M+Na+).

Preparation of Galβ1,3-(6-O-Ac)Galactal

A solution of 6-O-acetyl galactal (Compound 8; 72.3 mg, 0.38 mmol) and β-4-nitrophenyl galactopyranoside (Compound 1; 79.8 mg, 0.26 mmol) was prepared in PIPES-NaOAc-EDTA solution (3 mL) and acetone (100 μL) at 23° c. β-Galactosidase (E. coli, 75 U) was added, and the reaction mixture was maintained for 26 hours. The reaction mixture was purified (silica gel, 5:2:2 CHCl$_3$-MeOH-EtOAc) to afford Galβ1,3- (6-O-Ac galactal) (Compound 9; 38 mg, 42 percent) and recovered 6-O-acetyl galactal (39 mg, 54 percent).

$^1$H NMR (500 MHz, D$_2$O) δ6.49 (dd, J=1.8, 6.3 Hz, 1H, H-1 galactal), 4.92 (dt, J=1.9, 6.3 Hz, 1H, H-2 galactal), 4.67–4.66 (m, 1H, H-3 galactal), 4.60 (d, J=7.8 Hz, 1H, H-1 gal), 4.43–4.35 (m, 2H, H-6 galactal), 4.33 (dd, J=4.1, 8.1 Hz, 1H, H-5 galactal), 4.29–4.28 (m, 1H, H-4 galactal), 3.97 (br d, J=3.1 Hz, 1H, H-4 gal), 3.84–3.77 (m, 2H, H-6 gal), 3.56–3.73 (m, 1H, H-5 gal), 3.70 (dd, J=3.4, 9.9 Hz, 1H, H-3 gal), 3.69–3.63 (m, 1H, H-2 gal), 2.16 (s, 3H, C(O)CH$_3$). $^{13}$C NMR (125 MHz, D$_2$O) δ164.4, 144.7, 102.9, 102.9, 75.6, 74.6, 73.1, 73.1, 71.1, 69.1, 64.6, 61.4, 49.3, 20.7. HRMS (CI, NaI) m/e 373.1122 (373.1111 calcd for C$_{14}$H$_{22}$O$_{10}$Na, M+NA+).

The assignments for H-3 and H-4 of the galactal portion of the molecule were determined through DQF COSY $^1$H NMR studies as evidenced by long range coupling of H-1 (at δ6.49) with H-3 (at δ4.67–4.66) but not H-4 (at δ4.29–4.28).

The linkage was assigned based on the strong downfield shift of H-4 galactal to δ6 5.3 versus the slight shift of H-3 to δ6 4.5 upon peracetylation of the disaccharide. (These spectra were run in CDCl$_3$).

The foregoing is intended as illustrative of the present invention but not limiting. Numerous variations and modifications may be effected without departing from the true spirit and scope of the novel concepts of the invention.

We claim:

1. A process for producing a galactosylβ1,3glycal disaccharide that comprises admixing (i) a galactoside donor molecule, (ii) glucal, 6-O—C$_1$–C$_6$ acyl glucal or 6-O—C$_1$–C$_6$ acyl galactal as acceptor and (iii) a catalytic amount of β-galactosidase in an aqueous medium to form an admixture and maintaining the admixture so formed under biological reaction conditions for a time period sufficient to form said galactosylβ1,3glycal disaccharide.

2. The process according to claim 1 wherein said galactoside donor is an activated β-galactoside donor molecule.

3. The process according to claim 2 wherein said activated β-galactoside donor is p-nitrophenyl galactopyranoside.

4. The process according to claim 1 wherein said acceptor is glucal.

5. The process according to claim 1 wherein said acceptor is 6-O—C$_1$–C$_6$ acyl glucal.

6. The process according to claim 5 wherein said 6-O—C$_1$–C$_6$ acyl glucal is 6-O-acetyl glucal.

7. The process according to claim 1 wherein said acceptor is 6-O—C$_1$–C$_6$ acyl galactal.

8. The process according to claim 6 wherein said 6-O—C$_1$–C$_6$ acyl galactal is 6-O-acetyl galactal.

9. The process according to claim 1 including the further step of recovering said galactosylβ1,3glycal disaccharide.

10. A process for producing Galβ1,3-(6-O-Ac)Glucal that comprises admixing p-nitrophenyl galactopyranoside, 6-O-acetyl-glucal and a catalytic amount of β-galactosidase in an aqueous medium having a pH value of about 6.0 to about 8.0 at ambient room temperature to form a reaction mixture, and maintaining the reaction mixture for a time period sufficient for Galβ1,3(6-O-Ac)Glucal to form.

11. The process according to claim 10 including the further step of recovering said Galβ1,3(6-O-Ac)Glucal.

12. A process for producing Galβ1,3-(6-O-Ac)galactal that comprises admixing p-nitrophenyl galactopyranoside, 6-O-acetyl-galactal and a catalytic amount of β-galactosidase in an aqueous medium having a pH value of about 6.0 to about 8.0 at ambient room temperature to form a reaction mixture, and maintaining the reaction mixture for a time period sufficient for Galβ1,3(6-O-Ac)Glactal to form.

13. The process according to claim 12 including the further step of recovering Galβ1,3(6-0Ac)Galactal.

* * * * *